US005693344A

United States Patent [19]

Knight et al.

[11] Patent Number: 5,693,344
[45] Date of Patent: Dec. 2, 1997

[54] NON-HAZARDOUS PEST CONTROL

[75] Inventors: Arthur Michael Knight; Steven M. Bessette, both of Alpharetta, Ga.

[73] Assignee: Ecosmart, Inc., Roswell, Ga.

[21] Appl. No.: 553,475

[22] PCT Filed: May 20, 1994

[86] PCT No.: PCT/US94/05823

§ 371 Date: Nov. 9, 1995

§ 102(e) Date: Nov. 9, 1995

[87] PCT Pub. No.: WO94/27434

PCT Pub. Date: Dec. 8, 1994

Related U.S. Application Data

[63] Continuation-in-part of Ser. No. 65,594, May 21, 1993, Pat. No. 5,439,690.

[51] Int. Cl.$^6$ .......... A01N 59/00; A01N 59/06; A01N 35/00; A01N 37/10
[52] U.S. Cl. .......... 424/687; 424/405; 424/409; 424/489; 424/682; 424/686; 424/715; 424/716; 424/717; 514/533; 514/535; 514/536; 514/537; 514/544; 514/546; 514/690; 514/699; 514/701; 514/729; 514/730; 514/731; 514/738; 514/739; 514/951
[58] Field of Search .......... 424/687, 686, 424/715, 716, 717, 400, 405, 409, 489; 514/951, 533, 535, 536, 537, 544, 546, 690, 699, 701, 729-731, 738-739

[56] References Cited

U.S. PATENT DOCUMENTS

| | | | |
|---|---|---|---|
| 166,917 | 8/1875 | Davis | 424/646 |
| 2,423,284 | 7/1947 | Babbini | 424/628 |
| 3,159,536 | 12/1964 | Marotta | 424/600 |
| 4,834,977 | 5/1989 | Kohama et al. | 424/405 |
| 5,110,594 | 5/1992 | Morita | 424/405 |
| 5,186,935 | 2/1993 | Tucker | 424/405 |

FOREIGN PATENT DOCUMENTS 0462347  12/1991  European Pat. Off. .

OTHER PUBLICATIONS

Melchar, B. et al., "Evaluation of Physical Insecticides" Sci. Pharm., Proc., 25th, Butterworths, London, 1966; pp. 589-597.

Farm Chemicals Handbook '87, Meister Publishing Co., Willoughby, Ohio, 1987, p. C102, see "Dusts".

*Primary Examiner*—John Pak
*Attorney, Agent, or Firm*—Leonard Bloom

[57] ABSTRACT

A hazard-free method for controlling insects using a non-toxic composition. The invention includes a process for making the composition in the form of a fragrance and crystalline particles which puncture directly through the exoskeleton of an insect. In operation, the particles work themselves between the insect's protective body plates and then puncture the exoskeleton permitting entry of the fragrance into the body of the insect. Once inside, the particles absorb up to four times their weight of the vital body fluids of the insect and the fragrance has a neural effect on the insect.

20 Claims, 4 Drawing Sheets

# 5,693,344

NON-HAZARDOUS PEST CONTROL

This is a 371 application of PCT/US94/05823, filed on May 20, 1994, which is a continuation-in-part application of U.S. patent application Ser. No. 08/065,594, filed on May 21, 1993, now U.S. Pat. No. 5,439,690.

FIELD OF THE INVENTION

The present invention relates to the control of pests such as insects and, more particularly, to a non-hazardous pest control agent that eliminates pests through mechanical puncture of the exoskeleton and neural effects of a component entering the puncture.

BACKGROUND OF THE INVENTION

Insects and other pests have long plagued humankind. Over the years, various approaches have been taken to control pests and especially insects, and none have been completely satisfactory.

For example, the use of complex, organic insecticides, such as disclosed in U.S. Pat. Nos. 4,376,784 and 4,308,279, are expensive to produce, can be hazardous to man, domestic animals, and the environment, and frequently are effective only on certain groups of insects. Moreover, the target insects often build an immunity to the insecticide.

Another approach employs absorbent organic polymers for widespread dehydration of the insects. See, U.S. Pat. Nos. 4,985,251; 4,983,390; 4,818,534; and 4,983,389. However, this approach is limited predominantly to aquatic environments, and it likewise relies on hazardous chemical insecticidal agents. Further, the addition of essential oils is primarily as an insect attractant.

In addition, this approach is based on the selective absorption of a thin layer of insect wax from the exoskeleton and not to a puncture of the exoskeleton. [Sci. Pharm. Proc. 25th, Melchor et al, pp. 589–597 (1966)]

The use of inorganic salts as components of pesticides is reported by U.S. Pat. Nos. 2,423,284 and 4,948,013, European Patent Application No. 462 347, Chemical Abstracts 119(5):43357q (1993) and Farm Chemicals Handbook, page c102 (1987). These references disclose the inclusion of these components but not the puncturing of the exoskeleton of the insect by the salts.

The marketplace is replete with toxic chemical insecticidal agents that are offensive to apply and, more importantly, pose a danger to humans and the environment.

It would be greatly advantageous to solve these problems with an insecticidal agent that works mechanically and with a penetrating fragrance to kill pests, thereby eliminating the need for any toxic chemicals.

SUMMARY OF THE INVENTION

Accordingly, it is an object of the invention to provide a method for non-hazardous pest control and a composition for the same which kills pests mechanically and neurally.

It is another object to provide a safe, non-toxic pest control agent that will not harm the environment.

It is another object to provide a pest control agent that is highly effective in combating a wide variety of pests, including all insects having an exoskeleton.

It is another object to provide a pest control agent which has a pleasant scent, and which can be applied without burdensome safety precautions.

It is still another object to provide a pest control agent as described above which can be inexpensively produced.

It is yet another object of the invention to provide a pest control agent to which pests cannot build an immunity.

In accordance with the above-described and other objects, the present invention provides a method for delivering a pest control agent directly through the exoskeleton of an insect by applying a composition comprised of powdered crystals and a fragrance. The powdered crystals puncture the exoskeleton of the insect and penetrate therein. The puncture in the exoskeleton of the insect permits the entry into the insect's body of a fragrance which interferes with the body function of the insect. The method of the invention also encompasses killing the insect by dehydration using powdered crystals comprised of an alkaline metal carbonate, an alkali metal bicarbonate, and an absorbent material and neural effects of a fragrance.

Other advantages and results of the invention are apparent from a following detailed description by way of example of the invention and from the accompanying drawings.

DETAILED DESCRIPTION OF THE PREFERRED EMBODIMENT

Most insects have a waxy coating called their exoskeleton, or outer shell. The exoskeleton typically comprises multiple body plates joined together by cartilaginous membrane. This thin shell is the primary protection the insect has to insure the maintenance of its vital body fluids. If an insect loses as little as 10% of these fluids, it will die.

Figure 1:
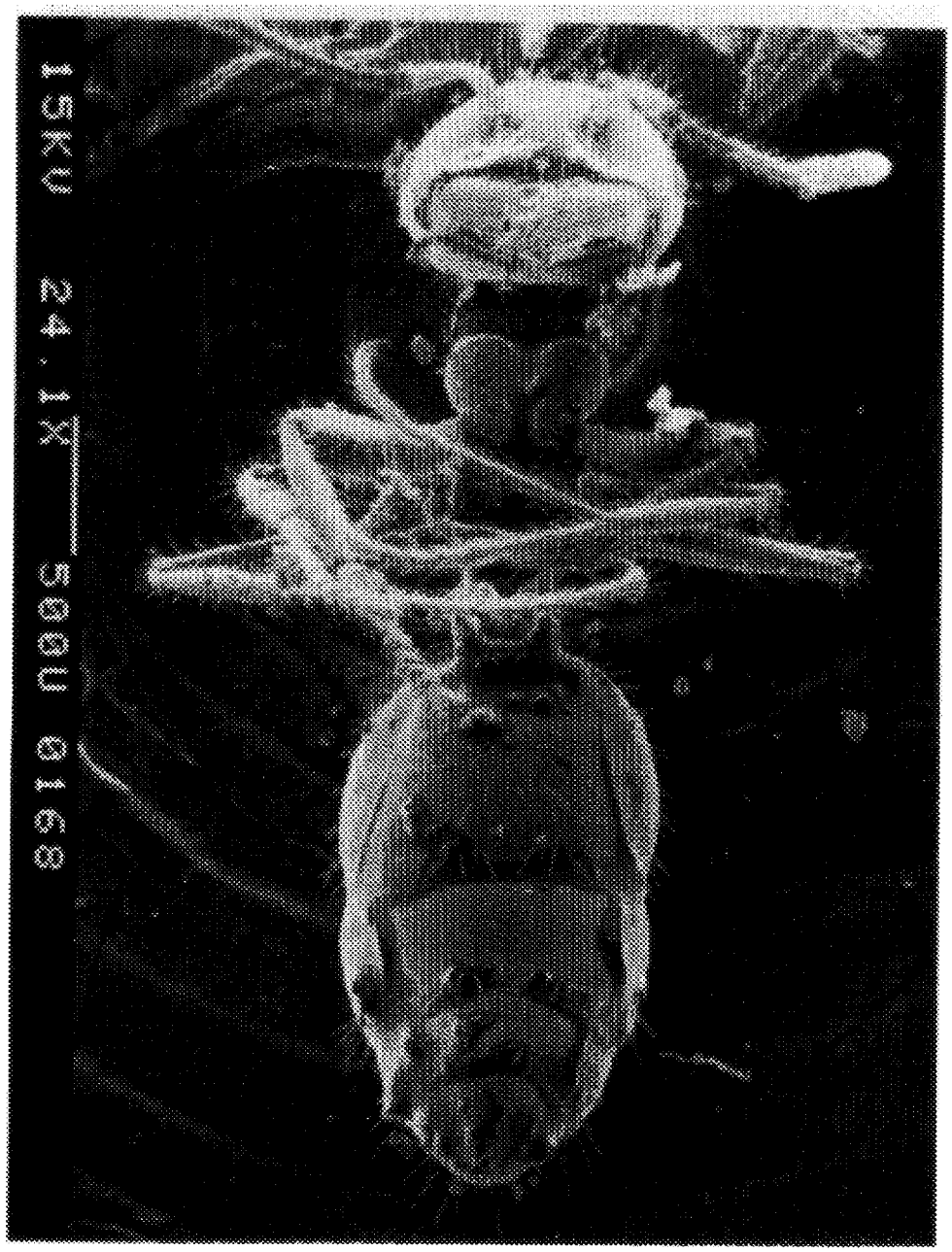
FIG. 1 is a photograph taken by a scanning electron microscope showing the underside of an ant with the crystalline particles of the present invention within and around the leg joints.

With particular reference to the drawings, FIG. 1 is a photograph taken by a scanning electron microscope showing the underside of an ant.

It can be seen that the exoskeleton provides absolute protection against most foreign agents such as pesticidal liquids and powders. For this reason, ingestion is the primary method of delivery for conventional pesticides. However, pests will only ingest certain substances and in small amounts. This imposes limits on the types of usable pesticides and their effectiveness. For instance, insects generally will not ingest fatal amounts of dehydrating pesticide.

The present invention proposes a new method of delivery of a pesticide directly through the exoskeleton. The composition and preparation of the present invention yields small 0.2–200 micron-sized crystalline particles.

FIG. 1 also shows the crystalline particles of the present invention in the vicinity of the ant legs. The crystalline particles are very small relative to the ant leg. Moreover, the particles are extremely sharp and abrasive by their crystalline nature. As an ant or other insect moves amongst the particles, the particles tend to work themselves between the insect's protective body plates, and they tend to pierce the exoskeleton.

Figure 2:
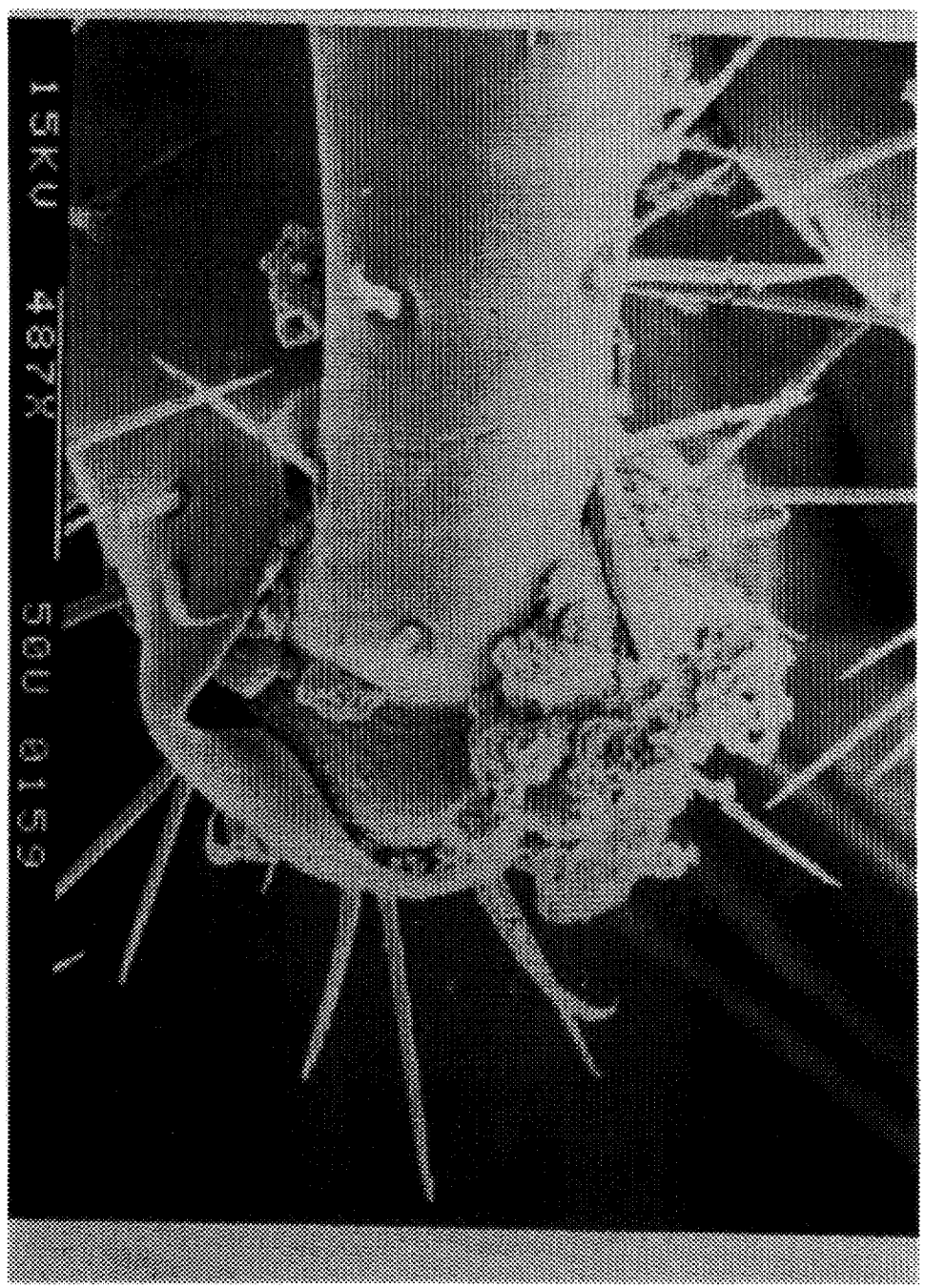
FIG. 2 is a photograph taken by a scanning electron microscope showing an enlarged view of a leg joint of FIG. 1 which further illustrates the crystalline particles as they invade the joint.

For example, FIG. 2 is an enlarged view of a leg joint in FIG. 1 which further illustrates the crystalline particles as they invade the joint. Movement of the joint causes the sharp crystalline particles to pierce and penetrate the exoskeleton.

Figure 3:
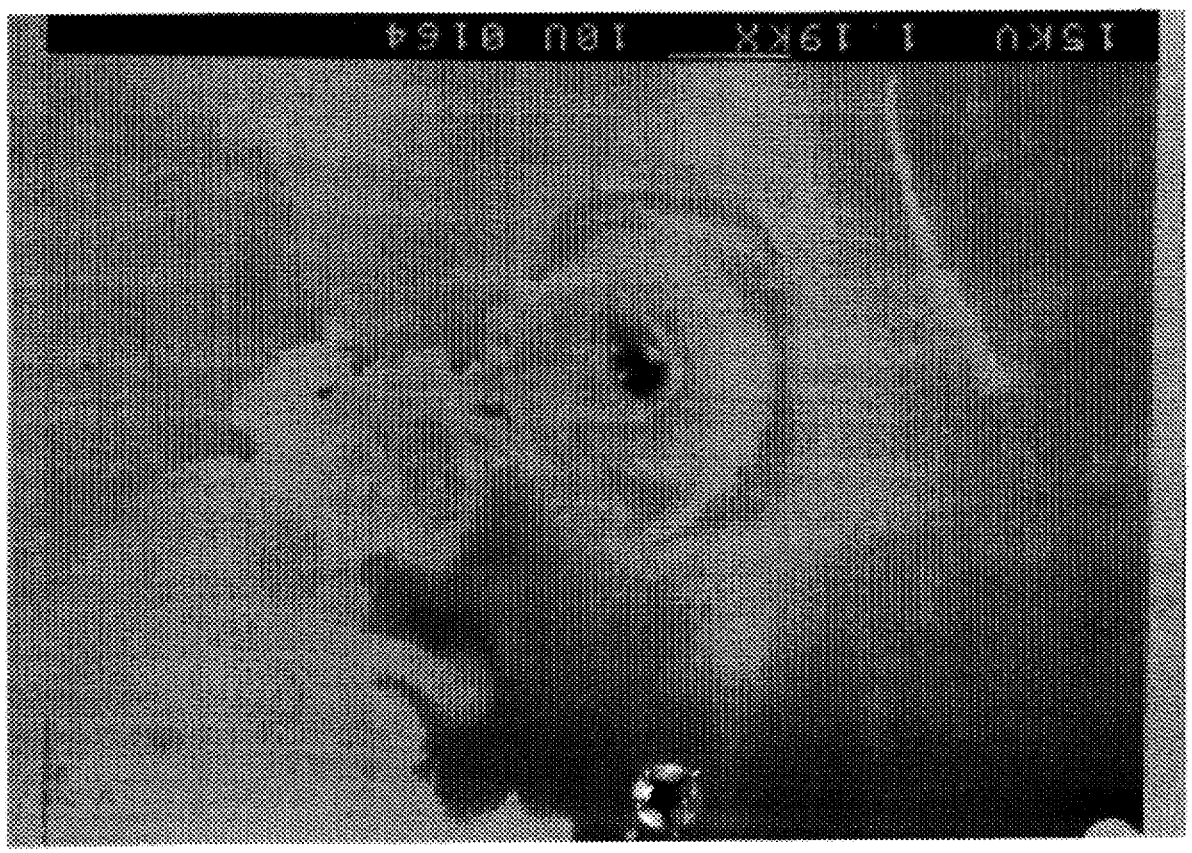
FIG. 3 is a photograph taken by a scanning electron microscope showing an enlarged view of a hole left in the thorax of an ant by operation of the crystalline particles of the present invention.

FIG. 3 shows an exemplary hole left in the thorax of an ant by operation of the crystalline particles.

Each particle can absorb up to four times its weight in liquid. Once the exoskeleton has been punctured, the particles begin to absorb the vital body fluids, ultimately causing death by dehydration. The invading particles can also migrate further into the internal body cavity of the insect, thereby interfering with breathing, digestion, reproduction, and/or body movements.

The fragrance component of the pesticide enters the body of the insect through the puncture and neurally effects the insect as will be described. Also the fragrance component affects the insect without entering the puncture in the exoskeleton of the insect. The fragrance is preferably a fragrance which also serves to attract the insects. The fragrance ranges from approximately 1–2% by weight of the insecticide. The following four fragrances have been found to be effective. The components are listed in their range of percentage by weight of the total weight of fragrance.

A floral fragrance having as its primary components amyl cinnamic aldehyde 1–5%, anisic aldehyde 1–5%, benzyl acetate 5–10%, cinnamic alcohol 5–10%, dipropylene glycol 10–20%, geraniol 1–5%, phenyl ethyl alcohol 1–5%, and terpineol 20–50%.

A floral fragrance having as its primary components benzyl acetate 1–5%, anisic aldehyde 1–5%, ionone 1–5%, methyl ionone 5–10%, diethyl phthalate 10–20%, amyl cinnamic aldehyde 1–5%, and dipropylene glycol 20–50%.

A potpourri fragrance having as its primary components amyl cinnamic aldehyde 1–5%, amyl salicylate 1–5%, benzyl acetate 10–20%, diethyl phthalate 10–20%, methyl anthranilate 1–5%, phenyl ethyl alcohol 1–5%, terpineol 10–15%, terpinyl acetate 1–5%, 4-tert butylcyclohexyl acetate 1–5%, and geraniol 1–5%.

A fresh fragrance having as its primary components benzyl acetate 5–10%, dipropylene glycol 20–50%, phenyl ethyl alcohol 1–5%, amyl cinnamic aldehyde 1–5%, and diethyl phthalate 10–20%.

None of the individual components are identified by the United States Environmental Protection Agency as having active insecticidal properties. All are considered to be inert. Thus, the demonstration of toxic effects on insects is considered to be unexpected.

If the pesticide of the present invention is liberally administered in the vicinity of the insects, it cannot be avoided by the insects and death is imminent. Moreover, it is impossible for the insects to build an immunity to the composition.

The process for production of the pesticide according to the present invention begins by mixing an alkaline earth metal carbonate, such as calcium carbonate, an alkali metal bicarbonate, such as sodium bicarbonate, a fragrance, and an absorbent material, such as diatomaceous earth. In addition, inert ingredients such as perlite may be added as desired in varying amounts for color and texture. Aside from the scenting agent, all of the above-mentioned ingredients are preferably mixed in powdered form.

The relative concentrations of the mixture are preferably about 30–35% alkaline earth carbonate, 60–65% alkali metal bicarbonate, 1–2% fragrance, and 4–5% absorbent material (all by weight). However, the individual constituents may vary within the following ranges while still achieving the desired result: 5–91% alkaline earth carbonate, 6–95% alkali metal bicarbonate, 1–93% scenting agent, and up to 90% absorbent material (all by weight).

The mixture is then boiled in water until the ingredients are dissolved (one to eight minutes boiling time). Sufficient water should be present to allow boiling and dissolution of the mixture. Preferably, the mixture is boiled at a concentration of about 1,224 grams of mixture per liter of water. The mixture can be stirred or otherwise agitated during boiling to help in dissolution.

After the mixture is boiled, it should be allowed to settle, thereby forming a bottom layer of sediment.

Once the mixture has settled, the water may be decanted or otherwise removed so as not to disturb the sediment layer. The sediment should not be disturbed because by this time crystals will have begun to grow.

After the water is removed, the residual sediment layer is dried. Drying may be accomplished by air, in a conventional microwave, or any other means so long as the sediment layer is not disturbed.

When the sediment is completely dry, it is ground to a powder. The granules of ground powder preferably have a size of under 100 microns.

The resulting product of the invention is a powdered crystalline composition capable of directly invading the exoskeleton of most insects by penetration therethrough. There are over one million species of insects including common pests such as ants, roaches, fleas, termites, and spiders. All are potential targets.

The following describes the process by which an exemplary batch of the pesticide was made and used.

A mixture was prepared using 60 parts (60%) powdered sodium bicarbonate, 33 parts (33%) powdered calcium carbonate, 2 parts (2%) potpourri fragrance oil, and 5 parts (5%) powdered diatomaceous earth.

The mixture was added to 10 ml of distilled water, and the suspension was boiled for eight minutes until the powdered mixture was completely dissolved. The solution was allowed to precipitate for fifteen minutes. Then the water was decanted and the bottom sediment layer was heated and dried in a microwave oven. The dried sediment was ground with a mortar, and this resulted in a particle size of about 0.1–100 microns.

A study was conducted to determine the insecticidal activity of the present invention against commonly found insects such as German cockroaches, cat fleas and Argentine ants. As described the term "dust" is used for the insecticide in a dry crystalline powder form and the term "powder" is used for dry formulations that are intended to be mixed with water.

TESTS WITH COCKROACHES

Continuous exposure tests.—The intrinsic insecticidal activity of the insecticide dust against B. germanica was determined by exposing cockroaches to fresh and aged deposits of the dust. Replicated groups of ten adult cockroaches from culture were confined to deposits of the dust, and its speed of action in terms of knockdown (KD) and paralysis was determined. Adult male cockroaches from culture were placed directly onto fairly heavy deposits of dust (1 to 1.2 cc) spread evenly on filter paper in covered 9-cm-diameter petri dishes. The time for irreversible KD to occur (KT) was determined from periodic, irregular observation. The insects were considered KD when they were on their back, or could be turned over, and could not right themselves within at least two minutes. KT-50 and KT-90 values (time for 50% and 90% KD, respectively) were calculated by interpolation of KD between times when data was collected; average KT value were obtained from the individual KD data. Comparison of KD activity was made with some commercial dust formulations including a non-fluorinated silica aerogel (SG-68), Drione™ (a fluorinated silica aerogel+pyrethrins), and a commercial diatomaceous earth (Celite™) applied and tested in the same manner.

The effects of atmospheric moisture and deposit age on the efficacy of the present insecticide dust were determined by the speed of action (KT) on cockroaches confined to deposits of the dust aged and tested at 98% (high) and 58% (moderate) relative humidity (RH). Average KT values were determined for fresh dust and for dust aged 2 weeks and 4 weeks. Cockroaches were exposed to 1 cc of dust in petri dishes, as described previously. Eighteen-mesh window screen covers on the dishes allowed for maintenance of the proper humidity and kept cockroaches from escaping from the damp dusts. For these tests dishes of dust were aged and tested on a wire mesh platform in saran-sealed aquaria. Enough dishes were prepared so that each deposit was tested only once. Water below the platform was used to maintain 98% RH, and a saturated aqueous sodium bromide solution was used to maintain 58% RH.

Choice box tests.—The activity and repellency of the present insecticide dust in a choice test was determined with standard two-compartment choice boxes.

Choice boxes are 12-in square, 4-in tall wooden boxes, with a tempered masonite floor. A vertical partition panel separates the box into two equal-sized compartments. A 0.5-in hole at the top center of the partition panel allows cockroaches to move from one compartment to the other. Transparent sheet plexiglass (0.125-in thick) taped to the top retains cockroaches in the box and allows observation of live and dead in each compartment. A piece of masonite keeps one compartment dark (dark compartment). The other compartment (light compartment) is exposed to normal room light conditions.

Five boxes were used for each treatment and the untreated control. For these tests 10 cc of test dust was spread evenly over the floor of the dark compartment and 20 adult male $B. germanica$ were released into the light compartment, where there was food and water. A cork in the partition hole was removed two hours later, when the cockroaches settled. Cockroaches prefer to aggregate in the dark, and they will normally readily move from the light compartment to the dark compartment of untreated choice boxes within a day or two. Once the partition cork was removed, the insects could move from the light compartment into treated dark compartment. The number dead and alive in each compartment of each box was recorded every few days. It was presumed that mortality was produced by contact with the insecticide in the dark, regardless of where the insects eventually died. Reluctance to move into the dark is attributable to the repellency of the treatment. Repellent treatments usually result in increased survivorship in the light compartment.

The mortality produced in choice boxes, and the position of cockroaches in relation to the treatment, provides a measure of the likely ultimate efficacy of a treatment when used under actual field conditions. In choice box tests, cockroaches are given an opportunity to encounter or avoid insecticide deposits. Highly toxic deposits may be ineffectual if cockroaches sense their presence and avoid lethal contact with them. On the other hand, slow-acting insecticides such as boric acid are effective in choice box tests because cockroaches readily walk on those deposits and are eventually killed by them.

TESTS WITH CAT FLEAS

Adult cat fleas, cultured under laboratory conditions were used in the study. Eggs collected from caged cats were reared through the larval period to adulthood on a special blood media. Adults used in the tests were approximately 2 to 3 days old (i.e., 2 to 3 days post-eclosion from the cocoon stage).

Speed of action of minimal deposits.—The rate of knockdown of fleas exposed to filter paper treated with the present insecticide dust and SG-68 silica aerogel was determined. Strips of No. 1 Whatman filter paper measuring 2 cm by 15 cm were submerged in the dusts and the excess shaken off. The lightly dusted strips were slipped into 2.5 cm-diameter by 15 cm tall glass test tubes and groups of fleas were directed from rearing emergence jars into the tubes. The open end of the tube was covered with parafilm. The tubes were left in a vertical position in a test tube rack. Because such a small amount of dust was used, all of it adhered to the paper and none could be seen on the surface of the test tubes. The fleas contacted the dust when they walked on the paper. Exposure to the dust was ensured because live fleas prefer the paper surface to the smooth surface of the test tube. Knockdown of fleas in the tubes was observed and recorded every few minutes until all the fleas were down. The fleas were considered KD if they were paralyzed at the bottom of the tube. Rate of KD (KT) was interpolated from the number of fleas KD at each time of observation.

Exposures on dusted carpet.—The minimum lethal dose and potential effectiveness of the present insecticide dust against fleas indoors was determined by exposing aliquots of fleas to a series of decreasing dosages of the dust on carpet. Dri-Die™ SG-68, a sorptive desiccant silica aerogel, was used as a comparative standard.

Weighed amounts of dust were sifted as evenly as possible onto the surface of 9-cm-diameter disks of new shag carpet at the bottom of 9 cm by 45-cm-tall plastic cylinders. The carpet was made of 100% nylon fibers and a jute backing. It has 9 double-stranded loops per $cm^2$, each strand being about 1.6 cm long.

The highest rate of dust applied was 1.2 cc/disk [14.2 cc/ft$^2$; that rate was successively halved and tested to the lowest rate of 0.06 cc/ft$^2$ (i.e., 9 rates tested)]. For exposure on each treatment rate, fleas from eclosion jars were directed onto the carpet, where they were confined for 24 hours. One or two replicates of 12 to 20 fleas were used for most rates, but 3 replicates were used for some rates. Because fleas cannot climb on the plastic or jump high enough to escape, they remained in contact with the carpet at the bottom of the cylinder. Untreated disks served as controls. Tests were conducted under ambient laboratory conditions (approximately 74° F. and 45% RH) and in an incubator cabinet at 98% RH.

The efficacy of the dust treatments was determined from the percentage of fleas that died within a 24-hour exposure period. Live and dead fleas on each disk were counted after tapping all the fleas from a disk into a basin of cool water. Live fleas move and swim vigorously. Fleas were considered dead if they sank, were immobile, or if they only had feeble, barely perceptible movement of their appendages.

Effect of humidity and volatility.—The specific application rate of 1.8 cc/ft$^2$ was used to compare the activity and volatility of the "active ingredient" in the present insecticide dust and some other dusts at ambient and 98% RH. Using the method described above, mortality at 24 hours was determined for fleas exposed to fresh insecticide, insecticide baked 48 hours at 250° F., diatomaceous earth, and silica aerogel. It was presumed that high temperature might drive off volatile actives, and that abrasive diatomaceous earth or sorptive non-fluorinated silica gel would provide greater kill at low humidity than at high humidity. Differences between rates of kill may indicate the mode of action of the insecticide dust.

TESTS WITH ARGENTINE ANTS

Based on the results obtained with the present insecticide in tests against cockroaches and fleas, Argentine ants were exposed to selected low doses of the dust as well as to comparative doses of SG-68 desiccant. Worker ants collected from a citrus grove were aspirated for study approximately 30 minutes before the test began. Aliquots of ants (11–15 for each of three replicates per treatment) were dumped onto lightweight deposits of the present insecticide dust and SG-68 spread evenly over the surface of filter paper waxed into the floor of 9-cm diameter glass petri dishes. Knockdown of the ants was observed every 5 minutes until all the ants in the treatments were down. An untreated set of papers served as a control series. The exposure tests provided an indication of the relative speed of action of the present insecticide and the SG-68 dusts against this species.

RESULTS AND DISCUSSION

Exposure of cockroaches to dust.—The irreversible knockdown (KD) of cockroaches exposed to fresh and aged deposits of the present insecticide at moderate and high humidities is summarized in Table 1.

TABLE 1

Knockdown of adult male German cockroaches confined to dust deposits aged and tested at high (98%) and moderate (58%) humidity.

| Treat-ment[a] | RH | Avg. hours for KD on deposits of indicated age | | | | | |
|---|---|---|---|---|---|---|---|
| | | Fresh | | 2 Weeks | | 4 Weeks | |
| | | KT-50 | KT-90 | KT-50 | KT-90 | KT-50 | KT-90 |
| Present insecticide | 58% | 0.3 | 0.6 | 0.3 | 0.7 | 0.3 | 0.7 |
| Silica gel | | 6.1 | 16.0 | 4.3 | 5.8 | 7.4 | 18.4 |
| Celite | | (39%)[b] | | (6%) | | (42%) | |
| Un-treated | | (0%) | | (0%) | | (16%) | |
| Present insecticide | 98% | 0.3 | 0.5 | 0.6 | 1.2 | 0.7 | 1.3 |
| Silica gel | | 6.7 | 12.3 | 8.3 | 17.3 | 13.3 | 21.9 |
| Celite | | (4%) | | (0%) | | (16%) | |
| Un-treated | | (0%) | | (0%) | | (13%) | |

[a]1 cc/9-cm-diam petri dish. Five replicates each with 10 cockroaches, were used for each exposure. Dusts spread onto Whatman No. 1 filter paper. Silica gel was SG-68 silica aerogel, an aerogel containing no fluoride. Celite is a commercial diatomaceous earth filter aid (Manville, Hyflow ™).
[b]Numbers in parentheses indicate total % KD at 24 hours, in instances where average KT-50 was not achieved.

The present insecticide dust provided rapid KD of German cockroaches, the average KT-50 being about 18 minutes, and 100% being down within about 40 minutes. Neither high humidity nor aging up to 4 weeks had a deleterious effect on its speed of action against cockroaches. Because even the most rapid-action desiccants require >30 minutes for KD, the effect observed with present insecticide suggests that the toxic action of the dust was not attributable solely to a sorptive ingredient. The affected cockroaches had curled or distended abdomens, and looked to be paralyzed as when toxified by a nervous system insecticide.

As expected, the non-fluorinated SG-68 desiccant took several hours to kill cockroaches, and was slightly less effective at high humidity. Typically, the desiccated cockroaches died standing upright, and did not show signs of tremors or paralysis.

Diatomaceous earth (like Celite™) alone is not usually considered to be an effective insecticide. Being an abrasive, the toxic action of diatomaceous earth occurs as a result of dusted insects slowly losing body water through abraded cuticle. Because moist air has little evaporative power, Celite™ was even less effective at high humidity.

Choice box tests with cockroaches.—Although the present insecticide dust provided rapid kill in continuous exposure tests, there was significant survivorship in the choice tests. There is usually a direct relationship between the speed of action of an insecticide and its repellency, and this relationship appears to have been confirmed in the choice box study. As shown in Table 2, deposits of the present insecticide dust provided mediocre kill of cockroaches in choice boxes, with 52% of the cockroaches being alive at 7 days and 40% alive at 14 days. Boric acid dust, on the other hand, provided 98% kill of cockroaches within a week.

Table 2 also shows that a high percentage of the live cockroaches in choice boxes treated with the present insecticide were always in the less-preferred light compartment, away from the dust. This was not so with boric acid, a non-repellent insecticide. Avoidance of the dust by survivors is characteristic of repellent insecticides such as silica gels (repellent by nature of their small particle size and sorptive properties) and fast-knockdown toxicants such as pyrethrins and pyrethroids.

TABLE 2

Activity and repellency of fresh dust deposits against German cockroaches, as measured in choice boxes.

| Dust[a] | % Mortality on day | | | % of live in light on day | | | Days for KD[b] | |
|---|---|---|---|---|---|---|---|---|
| | 1 | 7 | 14 | 1 | 7 | 14 | KT-50 | KT-90 |
| Present insecticide | 25 | 48 | 60 | 84 | 100 | 100 | 7.7 | — |
| Boric acid, tech. | 0 | 98 | 100 | 13 | 100 | — | 4.0 | 5.7 |
| Untreated | 0 | 3 | 10 | 12 | 3 | 18 | — | — |

[a]10 cc dust spread evenly over floor of dark compartment. For each dust, 3 replicates were tested, each with 20 adult male B. germanica.
[b]KT-50 and KT-90 are average days for 50% and 90% of the cockroaches to be irreversibly knocked down (KD).

The present insecticide dust, therefore, had high intrinsic insecticidal action against cockroaches, it had excellent activity at high and low humidity, and it retained activity for at least a month. The dust was, however, somewhat repellent, resulting in a high percentage of cockroaches surviving in choice tests. Direct application to cockroaches would certainly kill them.

Figure 4:
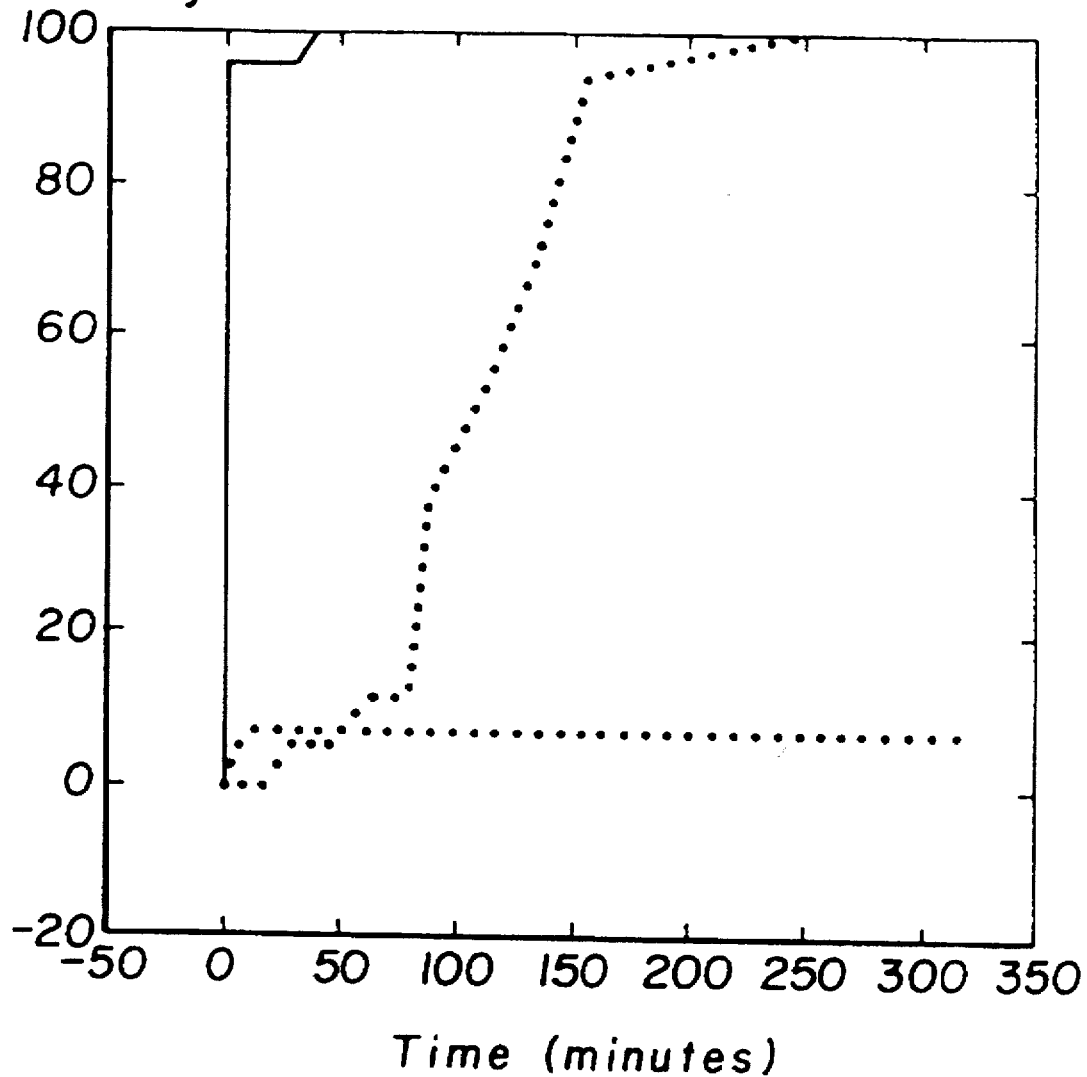
FIG. 4 is a graph of cumulative percent mortality vs. time for the knockdown of adult cat fleas for the present invention, silica gel desiccant and an untreated control.

Speed of action and minimum effective dose against fleas.—A low dose of the present insecticide dust provided very rapid knockdown of adult fleas. Its profile of activity against fleas is shown in FIG. 4. The cumulative mortality is plotted against knockdown time in minutes. The solid line represents the present insecticide, the dashed line represents SG-68 silica gel and the dotted line represents an untreated control. On paper in tubes it took nearly 4 hours for 90% knockdown of fleas on SG-68 silica gel, but less than 5 minutes for knockdown on the present insecticide. As with cockroaches, this rapid action suggests the presence of a nerve-involving insecticide rather than an adsorptive desiccant or an abrasive.

The good activity against fleas at a low does was substantiated in the series of exposure tests with successively lower doses of the present insecticide on carpet. As shown in Table 3, complete kill of fleas was achieved with as little as 0.2 cc/ft$^2$ of the present invention. Lower doses were not effective.

TABLE 3

Minimum effective dosages of fresh dust deposits on carpet against adult cat fleas, *Cunocephalides felis*.

| | % Mortality of fleas at 24 hours[a] | | | |
|---|---|---|---|---|
| | Present insecticide | | Silica gel (SG-68) | |
| Rate (cc/ft$^2$)[b] | Ambient RH | 98% RH | Ambient RH | 98% RH |
| 14.2 | 100 | 100 | 100 | 100 |
| 7.1 | 100 | 100 | 100 | 100 |
| 3.6 | 100 | 100 | 100 | 100 |
| 1.8 | 100 | 93.6 | 100 | 92.3 |
| 0.9 | 100 | 100 | 100 | 100 |
| 0.4 | 100 | 77.8 | 100 | 42.9 |
| 0.2 | 100 | 81.8 | 100 | 46.7 |
| 0.1 | 23.5 | — | 100 | — |
| 0.06 | 4.1 | — | 1.8 | — |
| Untreated | 9.7 | 11.3 | — | — |

[a]% mortality of treatments corrected with Abbott's formula to account for control mortality.
[b]Rates extrapolated from volume amounts applied to 78.5 cm$^2$ carpet discs. Highest rate applied (14.2 cc/ft$^2$) is equivalent to 1.2 cc/disc; other rates are proportional.

High humidity appeared to reduce the effectiveness of the dust at low rates of application as shown in Table 4.

TABLE 4

Effect of humidity on the activity of a low dose of dust deposit against adult cat fleas.

| | % Mortality at indicated RH[a] | |
|---|---|---|
| Dust treatment | Ambient | 98% |
| Present insecticide | 100 | 93.6 |
| Present insecticide (baked)[b] | 72.7 | 2.8 |
| Celite | 21.4 | 23.1 |
| Silica gel | 100 | 92.3 |
| Untreated | 5.6 | 6.4 |

[a]Fresh powders (1.8 cc/ft$^2$) applied to carpet. Fifteen to 20 fleas confined to treatments 24 hours. One to 2 replicates per treatment. Ambient humidity 25–40% RH.
[b]Heated 48 hours in hot-air oven at 250° F.

Surprisingly, the SG-68 also provided good kill at approximately the same low rates. Since SG-68 is a non-toxic desiccant, it could have concluded erroneously that the present insecticide dust also killed fleas by desiccating them. The much more rapid action found in the test tube assay suggests that there is a toxic component in the present insecticide formulation. The toxic component appears to involve toxification of the insect's nerves or cells.

Activity of the present insecticide against Argentine ants.—The rapid activity of the present insecticide against Argentine ants is shown in Table 5.

TABLE 5

Activity of minimal dust deposits against the Argentine ant, *Iridomyrmex humilis*.

| | Rate | % Dead at minutes of exposure | | | | | | Time for KD (min) | |
|---|---|---|---|---|---|---|---|---|---|
| Dust | (cc/ft$^2$) | 5 | 10 | 20 | 40 | 60 | 80 | KT-50 | KT-90 |
| Present Insecticide | 0.2 | 36 | 100 | | | | | 6.0 | 9.2 |
| | <0.06 | 23 | 32 | 100 | | | | 11.2 | 14.2 |
| SG-68 | 0.2 | 0 | 0 | 0 | 23 | 66 | 89 | 55.9 | 75.7 |
| | <0.06 | 0 | 0 | 0 | 24 | 84 | 100 | 49.5 | 60.3 |
| Untreated | — | 0 | 0 | 0 | 0 | 7 | 7 | — | — |

[a]Mortality based on 3 replicates, each with 11–15 worker ants.

The lightweight deposit (0.2 cc/ft$^2$) knocked down all the ants in less than 10 minutes; and an extremely light deposit (<0.06 cc/ft$^2$) provided effects that were nearly as rapid. The latter deposit was achieved by brushing a small amount of the dust onto the paper, and then tapping the remnant dust off the paper as the dish was inverted. Only a very small amount of dust remained. The SG-68 desiccant had a somewhat slower effect, resulting in high levels of KD within about 50 to 75 minutes. Desiccants such as SG-68 are active against ants such as these, perhaps because this ant has a relatively low percentage body water (<70%) and a large surface area compared to its body volume, a combination of which allows for rapid water loss from this insect.

As with the exposures of cockroaches and fleas, the ants contacting the present insecticide dust exhibited classic symptoms of neural toxication. Ants contacting the dust were quickly paralyzed. There was rapid running and apparent irritation before the onset of paralysis, a symptom often observed with ants exposed to finely divided dusts and fast-acting insecticides. There appeared to be less irritation among ants exposed to SG-68.

As with all dust formulations, care should be exercised to minimize airborne particulates of the dust at the time of application or afterwards. This may be more important if the dust is applied to carpet or furnishings for controlling fleas than if applied along baseboards, under appliances, or in other similar places for controlling cockroaches or ants.

The presence of a liable active component in the present insecticide formulation was somewhat verified when the activity of fresh insecticide was compared to that of heated (i.e., baked) insecticide. As shown in Table 4, the present insecticide baked 48 hours at 250° F. was less effective against fleas, and was significantly less effective when tested at high humidity. Baking apparently removed volatile active components or altered the configuration of the dust diluent. That removal or alteration reduced activity. Baking at higher temperature may reduce performance even more. Pyrethins and other botanical insecticides volatilize at 250° F.,but can reportedly be more quickly and thoroughly removed at 350° F.

The effectiveness compares favorably to conventional pesticides, yet the above-described product is primarily inorganic and completely non-hazardous to humans and other animals.

Although the non-hazardous nature of the product would be undermined, the product of the invention may also include a conventional insecticide, such as pyrethrin, which may be added during the boiling process. This serves to increase the effectiveness.

Having now fully set forth a detailed example and certain modifications incorporating the concept underlying the present invention, various other modifications will obviously occur to those skilled in the art upon becoming familiar with said underlying concept. It is to be understood, therefore, that within the scope of the appended claims, the invention may be practiced otherwise than as specifically set forth herein.

We claim:

1. A pesticide for insects comprising a carrier and a neurally effective fragrance, wherein said neurally effective fragrance is a chemical selected from the group consisting of amyl cinnamic aldehyde, amyl salicylate, anisic aldehyde, benzyl acetate, cinnamic alcohol, diethyl phthalate, dipropylene glycol, ionone, methyl anthranilate, methyl ionone, phenyl ethyl alcohol, terpinyl acetate, 4-tert butylcyclohexyl acetate, terpineol and mixtures thereof, wherein the neurally effective fragrance ranges from 1–2% of the total and further comprises amyl cinnamic aldehyde 1–5%, anisic aldehyde 1–5%, benzylacetate 5–10%, cinnamic alcohol 5–10%, dipropylene glycol 10–20%, geraniol 1–5%, phenyl ethyl alcohol 1–5%, and terpineol 20–50%, all by weight, wherein the carrier is a crystalline powder comprising 30–35% by weight of an alkaline earth metal carbonate, 60–65% by weight of an alkali metal bicarbonate and an absorbent material, and the carrier having a size in the range of 0.2 to 200 microns.

2. The pesticide of claim 1, wherein said alkaline earth metal carbonate is calcium carbonate.

3. The pesticide of claim 1, wherein said alkali metal bicarbonate is sodium bicarbonate.

4. The pesticide of claim 1, wherein said absorbent material comprises a diatomaceous material.

5. A method of applying the insecticide of claim 1 directly through the exoskeleton of the insect, comprising the step of applying the composition comprised of powdered crystals of the alkaline earth metal carbonate, the alkali metal bicarbonate and the absorbent material and the neurally effective fragrance, whereby said powdered crystals puncture the exoskeleton of said insect and penetrate therein, the neurally effective fragrance entering the punctured exoskeleton and neurally affecting the insect.

6. A pesticide for insects comprising a carrier and a neurally effective fragrance, wherein said neurally effective fragrance is a chemical selected from the group consisting of amyl cinnamic aldehyde, amyl salicylate, anisic aldehyde, benzyl acetate, cinnamic alcohol, diethyl phthalate, dipropylene glycol, ionone, methyl anthranilate, methyl ionone, phenyl ethyl alcohol, terpinyl acetate, 4-tert butylcyclohexyl acetate, terpineol and mixtures thereof, wherein the neurally effective fragrance ranges from 1–2% of the total and further comprises amyl cinnamic aldehyde 1–5%, amyl salicylate 1–5%, benzyl acetate 10–20%, diethyl phthalate 10–20%, methyl anthranilate 1–5%, phenyl ethyl alcohol 1–5%, terpineol 10–15%, terpinyl acetate 1–5%, 4-tert butylcyclohexyl acetate 1–5% and geraniol 1–5%, all by weight, wherein the carrier is a crystalline powder comprising 30–35% by weight of an alkaline earth metal carbonate, 60–65% by weight of an alkali metal bicarbonate and an absorbent material, and the carrier having a size in the range of 0.2 to 200 microns.

7. The pesticide of claim 6, wherein said alkaline earth metal carbonate is calcium carbonate.

8. The pesticide of claim 6, wherein said alkali metal bicarbonate is sodium bicarbonate.

9. The pesticide of claim 6, wherein said absorbent material further comprises a diatomaceous material.

10. A method of applying the insecticide of claim 6 directly through the exoskeleton of the insect, comprising the step of applying the composition comprised of powdered crystals of the alkaline earth metal carbonate, the alkali metal bicarbonate and the absorbent material and the neurally effective fragrance, whereby said powdered crystals puncture the exoskeleton of said insect and penetrate therein, the neurally effective fragrance entering the punctured exoskeleton and neurally affecting the insect.

11. A pesticide for insects comprising a carrier and a neurally effective fragrance, wherein said neurally effective fragrance is a chemical selected from the group consisting of amyl cinnamic aldehyde, amyl salicylate, anisic aldehyde, benzyl acetate, cinnamic alcohol, diethyl phthalate, dipropylene glycol, ionone, methyl anthranilate, methyl ionone, phenyl ethyl alcohol, terpinyl acetate, terpineol, 4-tert butylcyclohexyl acetate and mixtures thereof, wherein the neurally effective fragrance ranges from 1–2% of the total and further comprises benzyl acetate 1–5%, anisic aldehyde 1–5%, ionone 1–5%, methyl ionone 5–10%, diethyl phthalate 10–20%, amyl cinnamic aldehyde 1–5%, and dipropylene glycol 20–50%, all by weight, wherein the carrier is a crystalline powder comprising 30–35% by weight of an alkaline earth metal carbonate, 60–65% by weight of an alkali metal bicarbonate and an absorbent material, and the carrier having a size in the range of 0.2 to 200 microns.

12. The pesticide of claim 11, wherein said alkaline earth metal carbonate is calcium carbonate.

13. The pesticide of claim 11, wherein said alkali metal bicarbonate is sodium bicarbonate.

14. The pesticide of claim 11, wherein said absorbent material further comprises a diatomaceous material.

15. A method of applying the insecticide of claim 11 directly through the exoskeleton of the insect, comprising the step of applying the composition comprised of powdered crystals of the alkaline earth metal carbonate, the alkali metal bicarbonate and the absorbent material and the neurally effective fragrance, whereby said powdered crystals puncture the exoskeleton of said insect and penetrate therein, the neurally effective fragrance entering the punctured exoskeleton and neurally affecting the insect.

16. A pesticide for insects comprising a carrier and a neurally effective fragrance, wherein said neurally effective fragrance is a chemical selected from the group consisting of amyl cinnamic aldehyde, amyl salicylate, anisic aldehyde, benzyl acetate, cinnamic alcohol, diethyl phthalate, dipropylene glycol, ionone, methyl anthranilate, methyl ionone, phenyl ethyl alcohol, terpinyl acetate, terpineol, 4-tert butylcyclohexyl acetate and mixtures thereof, wherein the neurally effective fragrance ranges from 1–2% of the total and further comprises benzyl acetate 5–10%, dipropylene glycol 20–50%, phenyl ethyl alcohol 1–5%, amyl cinnamic aldehyde 1–5%, and diethyl phthalate 10–20%, all by weight, wherein the carrier is a crystalline powder comprising 30–35% by weight of an alkaline earth metal carbonate, 60–65% by weight of an alkali metal bicarbonate and an absorbent material, and the carrier having a size in the range of 0.2 to 200 microns.

17. The pesticide of claim 16, wherein said alkaline earth metal carbonate is calcium carbonate.

18. The pesticide of claim 16, wherein said alkali metal bicarbonate is sodium bicarbonate.

19. The pesticide of claim 16, wherein said absorbent material comprises a diatomaceous material.

20. A method of applying the insecticide of claim 16 directly through the exoskeleton of the insect, comprising the step of applying the composition comprised of powdered crystals of the alkaline earth metal carbonate, the alkali metal bicarbonate and the absorbent material and the neurally effective fragrance, whereby said powdered crystals puncture the exoskeleton of said insect and penetrate therein, the neurally effective fragrance entering the punctured exoskeleton and neurally affecting the insect.

* * * * *